United States Patent
English et al.

(10) Patent No.: US 9,849,303 B2
(45) Date of Patent: Dec. 26, 2017

(54) CARTRIDGE, MEDICAL APPARATUS AND METHOD

(75) Inventors: Stuart English, Alnwick (GB); Richard Anthony Kirk, London (GB); Martin Neil Holland, Maidenhead (GB)

(73) Assignee: Polyphotonix Limited, Sedgefield, County Durham (GB)

( * ) Notice: Subject to any disclaimer, the term of this patent is extended or adjusted under 35 U.S.C. 154(b) by 687 days.

(21) Appl. No.: 14/004,882

(22) PCT Filed: Feb. 22, 2012

(86) PCT No.: PCT/GB2012/050397
§ 371 (c)(1),
(2), (4) Date: Sep. 12, 2013

(87) PCT Pub. No.: WO2012/123709
PCT Pub. Date: Sep. 20, 2012

(65) Prior Publication Data
US 2014/0005757 A1    Jan. 2, 2014

(30) Foreign Application Priority Data

Mar. 15, 2011 (GB) .................................. 1104369.2
Oct. 3, 2011 (GB) .................................. 1116936.4

(51) Int. Cl.
*A61N 5/06* (2006.01)

(52) U.S. Cl.
CPC ............. *A61N 5/0613* (2013.01); *A61N 5/06* (2013.01); *A61N 2005/0648* (2013.01)

(58) Field of Classification Search
CPC .... A61N 2005/0632; A61N 2005/0645; A61N 2005/0647; A61N 2005/0658; A61N 5/06; A61N 5/0613
(Continued)

(56) References Cited

U.S. PATENT DOCUMENTS

| 4,372,318 A | 2/1983 | Viesturs et al. |
| 4,396,259 A | 8/1983 | Miller |

(Continued)

FOREIGN PATENT DOCUMENTS

| CN | 1091947 A | 9/1994 |
| CN | 101938935 A | 1/2011 |

(Continued)

OTHER PUBLICATIONS

Search Report under Section 17, United Kingdom Intellectual Patent Office, for Application No. GB1104369.2, dated Dec. 1, 2011 (1 page).
(Continued)

*Primary Examiner* — John R Downey
(74) *Attorney, Agent, or Firm* — Klarquist Sparkman, LLP (57) ABSTRACT

A cartridge, medical apparatus and method are disclosed. The cartridge and a holding element are for operable connection with each other to form a phototherapy apparatus. The cartridge includes a radiation source for emitting radiation towards an area to be treated of a user; a mount element for positioning the radiation source in a predetermined position relative to the area to be treated; wherein the mount element comprises a locating portion configured for locating the cartridge at a predetermined position with respect to a body portion of the user.

12 Claims, 4 Drawing Sheets

(58) Field of Classification Search
USPC .......................................... 606/4; 607/88–91
See application file for complete search history.

(56) References Cited

U.S. PATENT DOCUMENTS

| | | | |
|---|---|---|---|
| 5,274,865 A | 1/1994 | Takehashi | |
| 5,628,772 A | 5/1997 | Russell | |
| 2003/0014096 A1 | 1/2003 | Burkheart | |
| 2003/0195383 A1 | 10/2003 | Yon | |
| 2004/0162549 A1* | 8/2004 | Altshuler | A61B 18/203 606/9 |
| 2005/0278003 A1 | 12/2005 | Feldman | |
| 2006/0259100 A1 | 11/2006 | Hilburg | |
| 2007/0002692 A1 | 1/2007 | Van Brunt | |
| 2008/0147149 A1 | 6/2008 | Pannu | |
| 2008/0251085 A1 | 10/2008 | Schwebel | |
| 2009/0018622 A1* | 1/2009 | Asvadi | A61N 5/0621 607/91 |
| 2009/0192437 A1 | 7/2009 | Soltz et al. | |
| 2009/0260633 A1 | 10/2009 | Vreman | |

FOREIGN PATENT DOCUMENTS

| | | |
|---|---|---|
| CN | 201543118 U | 8/2011 |
| GB | 2410903 A | 8/2005 |
| JP | 2003-305017 | 10/2003 |
| JP | 2006-525039 | 11/2006 |
| WO | WO2004/096364 A1 | 11/2004 |
| WO | WO2010/076706 A1 | 7/2010 |
| WO | WO2010/076708 A1 | 7/2010 |
| WO | WO2010/122434 A1 | 10/2010 |
| WO | WO2011/135362 A1 | 11/2011 |

OTHER PUBLICATIONS

Further Examination Report, New Zealand Intellectual Property Office, for Application No. 616569, dated Dec. 3, 2014 (3 pages).
International Preliminary Report on Patentability and Written Opinion of the International Searching Authority, dated Sep. 17, 2013, for corresponding International Application No. PCT/GB2012/050397, 8 pages.
International Search Report and Written Opinion of the International Searching Authority, dated Jun. 18, 2012, for corresponding International Application No. PCT/GB2012/050397, 12 pages.
Notification of the First Office Action and Search Report (with English translation) from the State Intellectual Property Office of People's Republic of China for corresponding Chinese Application No. 201280020752.3, dated Jun. 17, 2015, 17 pages.
Office Action (English translation only) from Japan Industrial Property Office, for corresponding Japanese Patent Application No. 2013-558496, dated Feb. 22, 2016, 5 pages.

* cited by examiner

CARTRIDGE, MEDICAL APPARATUS AND METHOD

CROSS REFERENCE TO RELATED APPLICATIONS

This is the U.S. National Stage of International Application No. PCT/GB2012/050397, filed Feb. 22, 2012, which in turn claims the benefit of and priority to Great Britain Patent Application Nos. GB1104369.2, filed Mar. 15, 2011 and GB1116936.4, filed Oct. 3, 2011.

The present invention relates to a cartridge, medical apparatus and method. In particular but not exclusively the invention relates to an illuminating cartridge and complementary holding element used in the treatment of eye diseases, such as, diabetic retinopathy and macular degeneration.

Phototherapy has been used for various therapeutic and cosmetic purposes. It generally involves the use of specific wavelengths of light radiation being administered to a patient. Phototherapy may be used to treat chronic infections such as hepatitis (A, B or C), bacterial infections, wounds, precancer conditions, seasonal affective disorder (SAD), various dermatological and cosmetic purposes such as skin rejuvenation, and various eye diseases such as diabetic macular edema, retinopathy of prematurity, wet or dry age-related macular degeneration and diabetic retinopathy, for example.

Diabetic retinopathy is a condition in which damage to the retina in the eye occurs and is caused by diabetes. More specifically, diabetic retinopathy is the result of microvascular retinal changes where hyperglycemia-induced intramural pericyte death and thickening of the basement membrane cause damage to the wall of blood vessels in the eye. This damage changes the formation of the blood-retinal barrier and also makes the retinal blood vessels become more permeable. Small blood vessels, such as those in the eye, are particularly vulnerable to poor blood sugar control. An overaccumulation of glucose and/or fructose damages the blood vessels in the retina. Damaged blood vessels are likely to leak fluid and lipids onto the macula. This condition can therefore lead to impaired vision and ultimately blindness. The condition can be treated by preventing the complete dark adaptation of the eye by providing some degree of light radiation to the eyes or eyelids during sleep. This is because, during dark adaptation, the eye requires an increased oxygen level, and thus the blood vessels must work harder during dark adaptation. Therefore by preventing complete dark adaptation of the eye, the blood vessels are less stressed and can rejuvenate over time. For diabetic retinopathy, preferably light having a wavelength of between around 460 to 550 nm is administered to the eyes or eyelids, which corresponds to the scotopic sensitivity of the eye.

It has been found useful to administer the radiation to the eye area by providing a mask type of device for a patient to wear during sleep, the mask configured to be secured over the patient's head to cover the eye area, and adapted to include light emitting sources in the region of the eyes. The light sources may be LEDs or OLEDs, for example, and are arranged to emit light towards the eye area.

Light treatment masks are generally worn whilst the user is sleeping or dozing and direct a controlled light source towards the user's eye or eyes. Light treatment masks can be used to treat a variety of ailments including migraine, seasonally adjusted disorder, macular degeneration and diabetic retinopathy. An example of such a light mask is described in GB2410903, WO2005/079716 and WO2010/076706. Some light treatment masks variants are also used to aid sleeping and to wake the user in a controlled and natural way.

The 'Kelvin Vision Light Mask' (www.kelvinvision.com) is another example of a known light mask.

Other disclosed devices include a programmable mask for waking an individual (US2007/002692). This is a mask-like apparatus that includes a programmable controller for light emitting diodes (LEDs) which are positioned to illuminate the eye area of the user. The controller is battery powered. Illumination intensity profiles are used to control the level of intensity of the illumination to create a time-phased increase in intensity that wakes the user gradually.

Electroluminescent light therapy devices such as described in US2005/278003 are wearable devices that may be in the form of a hat or cap, eyeglasses, an eye mask, or a face mask. They deliver light from light-emitting diodes or deliver electroluminescent light from a light source powered by an inverter connected to the hat or cap, the eyeglasses, the eye mask, or the face mask. The delivery of the light is for entertainment or therapeutic purposes. Delivery of therapeutic light to the retinal area or to the skin of the user by a wearable device, without the use of the hands of the user, applies consistent levels of the therapeutic light to relax the user, to remove wrinkles in the skin, and to impart other healing effects. A sufficient amount of lux at appropriate optical wavelengths is generated to be incident for long periods upon the retina of the user or upon the skin of the user for healing effect.

A disposable sleep mask for treating dry eye syndrome is described in US2008/0251085. This mask aims to ameliorate the effects of dry eye syndrome in a dry eye subject, including a thin, flexible, substantially water vapour impermeable membrane having two opposed eye covering portions separated by a central portion. The central portion is gathered to create a shape that accommodates nose structure of the dry eye subject and curves the opposed eye covering portions to conform the opposed eye covering portions generally to the curvature of the dry eye subject's face in an area surrounding the dry eye subject's eyes. The mask further includes an absorbent structure securable between the impermeable membrane and the eyes of the user that is capable of absorbing and via the means of evaporation releases a substance to improve the comfort and health of the eyes for the dry eye syndrome subject.

However, the above-described devices suffer from various drawbacks, which may prevent the most effective use of the apparatus by a user. For example, the devices described above are generally quite bulky in shape and would therefore be likely to interfere with a user's sleep if they naturally move their head during the period of sleep. The devices described above also have a high weight. This may lead to waking of the user and/or movement of the device out of its ideal position over the eye area. This also makes the devices difficult to transport around with a user when travelling. The above-described devices may have wiring to connect the mask to a power source, which again could interfere with a user's sleep, or even be dangerous if tangled.

The present invention seeks to at least partly mitigate the above-mentioned problems.

According to a first aspect of the present invention there is provided a cartridge for operable connection with a holding device to form a phototherapy apparatus, the cartridge comprising:

a radiation source for emitting radiation towards an area to be treated of a user;

a mount element for positioning the radiation source in a predetermined position relative to the area to be treated;

wherein the mount element comprises a locating portion configured for locating the cartridge at a predetermined position with respect to a body portion of the user.

According to a second aspect of the present invention there is provided a holding element for operable connection with a cartridge to form a phototherapy apparatus, the holding element comprising:

a body portion arranged to hold a cartridge for emitting radiation towards an area to be treated of a user;

a securing element for securing the holding element against the user;

a locating portion configured for locating the holding element at a predetermined position with respect to a body portion of the user.

According to a third aspect of the present invention there is provided a kit of parts comprising the cartridge of the first aspect and the holding element of the second aspect.

According to a fourth aspect of the present invention there is provided an assembly comprising:

a cartridge comprising a radiation source for emitting radiation towards an area to be treated of a user; a mount element for holding the radiation source; wherein the mount element comprises a locating portion configured for locating the cartridge at a predetermined position with respect to a body portion of the user; and a holding element for operable connection with the cartridge, comprising a body portion arranged to hold the cartridge in a predetermined position relative to the area to be treated, a securing element for securing the holding element against the user, and a locating portion configured for locating the holding element at a predetermined position with respect to the body portion of the user.

According to a fifth aspect of the present invention there is provided an assembly for delivering light radiation to a patient, comprising the cartridge of the first aspect and the holding element of the second aspect.

According to a sixth aspect of the present invention there is provided a method of delivering light radiation to an area to be treated of a user comprising providing a cartridge of the first aspect, securing the cartridge to a user with a holding element, and delivering a predetermined dosage of light radiation to the user.

According to the present invention there may be provided a replaceable light treatment cartridge held on the face of a user by means of a separate attachment device (holding element) such as a mask. The cartridge incorporates means to illuminate in the direction of the eye and has a self-contained power source, allowing for continuous periods of use in excess of 4 hours. In certain embodiments of the invention the apparatus may be used in a series of measured dosages, for example for 8 hours per day over a period of one month, without needing to change or recharge the power source. Of course the dosage supplied will depend upon the treatment instructed by a doctor or physician or other instructing party. When the attachment device and cartridge are used in combination one or more light source is automatically located within the orbit of one or more eye and in relation to the bridge of the nose of the user. Hence the device, and therefore the light emitted, remains in place during sleep ensuring no harm is caused to the user.

Certain embodiments of the present invention provide the advantage that the cartridge element is replaceable and reusable. This allows the cartridge, which holds the electronic components of the apparatus, to be detached from the holding element, which provides the means of attachment to the user. This enables the holding element to be periodically washed by the user so as to avoid a build-up of body tissue or secretions, or even avoid diseases such as conjunctivitis.

Certain embodiments of the present invention provide the advantage that different cartridges may be prescribed to the user at certain times by a doctor or physician or other instructor so as to provide respective different treatment regimes to the user. As such, the radiation dosage for a specific user/patient may be clearly and effectively delivered and monitored.

Certain embodiments of the present invention provide the advantage that the replaceable cartridge allows the cartridge and holding element to be manufactured, distributed and sold separately. This may help to increase the environmentally friendliness of the apparatus as a whole.

Each of the cartridge and holding element may be thin and flexible so as to give minimal disturbance to a user's sleep pattern during wear. By providing the cartridge and holding element in a substantially planar form, this helps to reduce the bulkiness of the apparatus.

Certain embodiments of the present invention provide the advantage that the locating portion of the cartridge and/or holding element helps to locate the apparatus at a predetermined position with respect to a body portion of the user. This may also help to locate the cartridge and holding element with respect to each other.

Certain embodiments of the present invention provide the advantages that:

1) A slim profile that fits to the face without protruding so that the user can comfortably sleep with it on.

2) Onboard power, eliminating the need for a cable that could be snagged or harm the user whilst they are asleep (e.g. through strangling).

3) Means to replace the cartridge. The cartridge is held on the face by means of a separate attachment device, this means that the cartridge can be easily replaced when it runs out of power.

Embodiments of the invention will now be described by way of example with reference to the accompanying drawings, in which.

In the drawings like reference numerals refer to like parts.

Figure 1:
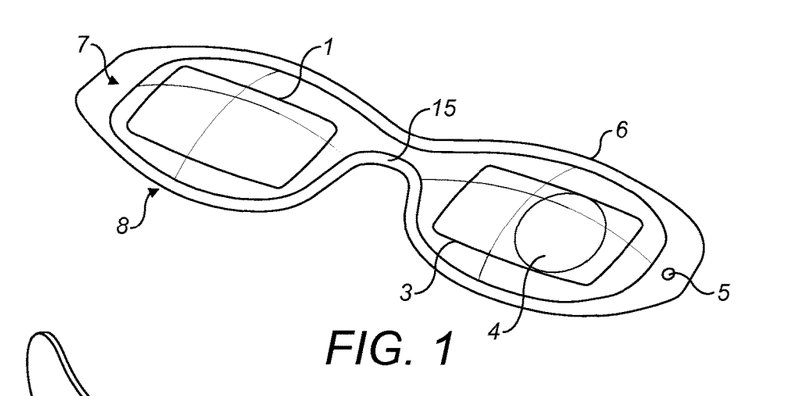
FIG. 1 illustrates a perspective view of a replaceable cartridge incorporating two light sources.
Figure 2A:
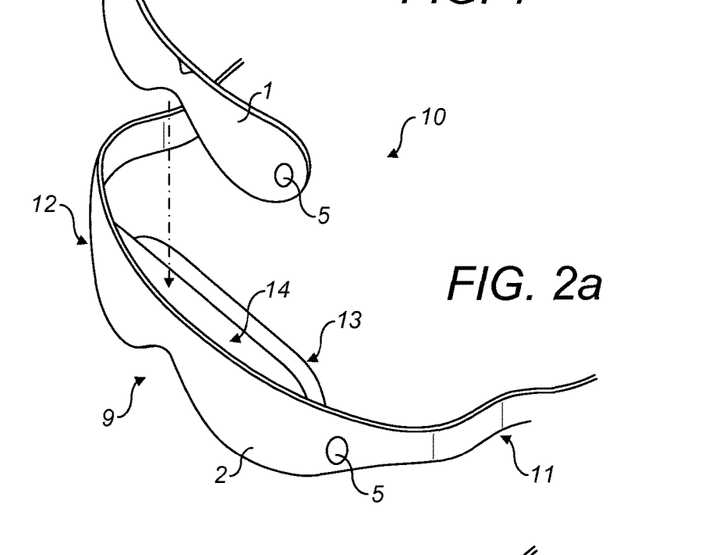
FIG. 2a illustrates a perspective view of a holding element and cartridge.
Figure 2B:
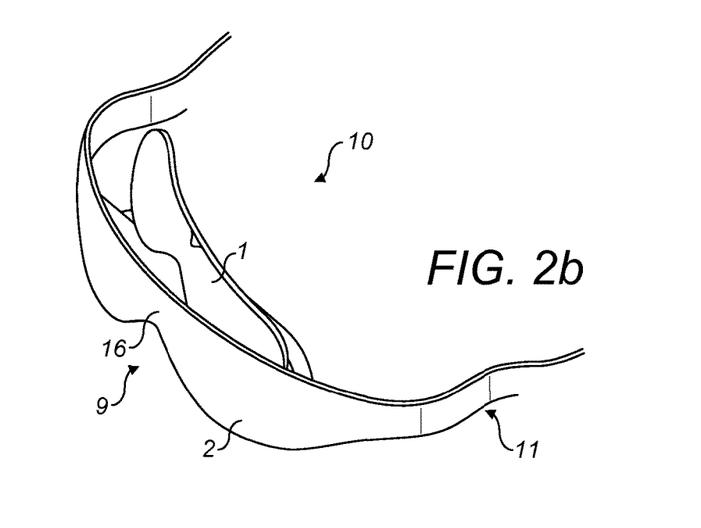
FIG. 2b illustrates another perspective view of a holding element and cartridge.

A replaceable/removable cartridge (1) of the present invention is shown in FIG. 1. The cartridge may be inserted and held in a holding element (2) that can be releasably fixed to (i.e. positioned onto or adjacent to) the head of a user. The cartridge (1) and holding element (2) form a phototherapy apparatus (10) for providing light radiation to an area to be treated (in this case a user's eyes), as shown in FIGS. 2a and 2b. In this embodiment the apparatus (10) is formed as a mask type of apparatus for placing over a user's head.

Referring again to FIG. 1, the cartridge includes a mount element (6) suitable for holding the various components needed for the functioning of the device. The mount element is generally planar, having a small width so as to enable the apparatus to be as thin and compact as possible. The mount element should aptly be of a width that enables the cartridge to be robust enough to allow handling by a user or physician and wearing by a user without easy breakage, yet compact enough to fit against a user's face as neatly and non-invasively as possible. Of course, the material that the mount is formed from will also determine the robustness of the mount element. In this embodiment the mount element is formed from a moulded or formed polymer, though the mount element could be formed from any other suitable material and/or production technique. This mount element is also flexible to enable a degree of moulding to the face shape of the user. The mount element also has a front surface (7), and a rear surface (8) opposed to the front surface. The rear surface will be positioned close to a user's face and eyes, in use. As can be seen from FIG. 1, the mount element is aptly formed in the general shape of two conjoined ovals, similarly to a pair of glasses, to generally correspond to a user's eye area.

The cartridge (1) provides one or more sources of illumination (3), i.e. a radiation source, for directing light radiation towards one or more eye of a user. In this embodiment the radiation source is an OLED that is mounted onto the rear surface of the mount element. The radiation source (3) or each radiation source may be positioned in or on a support structure or mount so as to be placed in a predetermined position relative to a patient's eye (or other area to be treated).

It has been found that OLEDs emitting radiation within the range 460 nm to 550 nm, centred at 480 nm to 500 nm, are particularly suitable for treatment of diabetic retinopathy. This is because when the radiation is filtered through the eyelids of a patient who is asleep, radiation centred at 510 nm reaches the retinas of the patient, which is particularly efficacious for the treatment of diabetic retinopathy. Of course other ranges of wavelengths or light radiation are known to be useful to treat other conditions. It will also be appreciated that the dosage regime for light radiation will also likely include the time period for which radiation treatment occurs, the frequency of the periods, and luminance of the light radiation (measured by candela per metre squared—$cd/m^2$). Other conditions will of course require different dosage regimes (e.g. age-related macular degeneration may require a wavelength of around 670 nm).

In this embodiment the cartridge incorporates an on-board power supply (4) that can be switched on/off in long cycles by means of two switches (5). In one embodiment, in order to switch the cartridge on, both switches may be depressed simultaneously. The power supply (4) is a flexible lithium battery that again may be substantially planar in design. Of course any source of power may be used, for instance a power supply that is charged through induction, electrochemical storage and release, or a solar cell that is integral or separate to the apparatus. The battery (4) is coupled to the radiation source(s) (3) so as to enable the supply of power. The radiation source (3) may be coupled to a processor (not shown) so as to control the operation of the radiation source, e.g. to turn the radiation source (3) on and off in accordance with a prescribed treatment regime. The cartridge may optionally further comprise a memory (not shown) coupled to the processor. The memory may be arranged to store instructions for controlling the processor and data relating to the treatment regime, for instance intensity of radiation emitted by the radiation source (3).

The holding element (2) of the present embodiment is illustrated in FIGS. 2a and 2b. The holding element is generally shaped in the form of a facial mask and includes a main body portion (9) and a strap portion (11) for securing the apparatus to the user. The strap portion may be a single expandable strap or a pair of straps that fasten to the user's ears or to each other, for example. The strap portion (11) extends from each end of the main body portion (9).

The main body portion (9) includes a front body portion (12) and a rear body portion (13) that are joined at side and lower areas to form a pouch or pocket (14) there between. The rear body portion (13) is the portion facing the user's skin, in use. The pouch (14) is shaped and sized to match the cartridge (1). The front and rear body portions (12,13) are substantially planar, aptly flexible, and similarly to the cartridge, of a width that enables the cartridge to be robust enough to allow handling by a user or physician and wearing by a user without easy breakage, yet compact enough to fit against a user's face as neatly and non-invasively as possible. In this embodiment the front and rear body portions (12,13) are formed of a foam material from a moulded or formed polymer, though the body portions could be formed from any other suitable material and/or production technique.

In this embodiment the rear body portion (13) has a pair of voids (not shown) corresponding to the eye areas of a user, such that radiation emitted by the OLEDs on the inserted cartridge may be directly received by the user. Alternatively, the rear body portion could be formed from a transparent material, for example, so as to allow light radiation to reach the area to be treated.

As shown in FIGS. 2a and 2b, the cartridge (1) is removably insertable into the holding element (2) by placing the cartridge (1) into the open pouch (14). In other embodiments the pouch may be sealable so as to help prevent the cartridge from escaping during use. This may be achieved with hook and loop material at the open edge of the pouch, for example.

Each of the cartridge (1) and holding element (2) includes a locating portion (15,16) for locating them at a predetermined position with respect to the nose bridge of the user. More specifically, in this embodiment the locating portion (15) of the cartridge (1) is an area of the cartridge that is configured (shaped and sized) so as to enable the cartridge to be locatable against, and fit comfortably next to, the user's nose bridge. The locating portion of the holding element (2) is an area of the holding element that is configured so as to enable the holding element (2) and apparatus (10) to be locatable against, and fit comfortably next to, the user's nose bridge. In addition, the locating portions (15,16) also help to locate the cartridge (1) with respect to the holding element (2), by virtue of their corresponding configurations.

Figure 3:
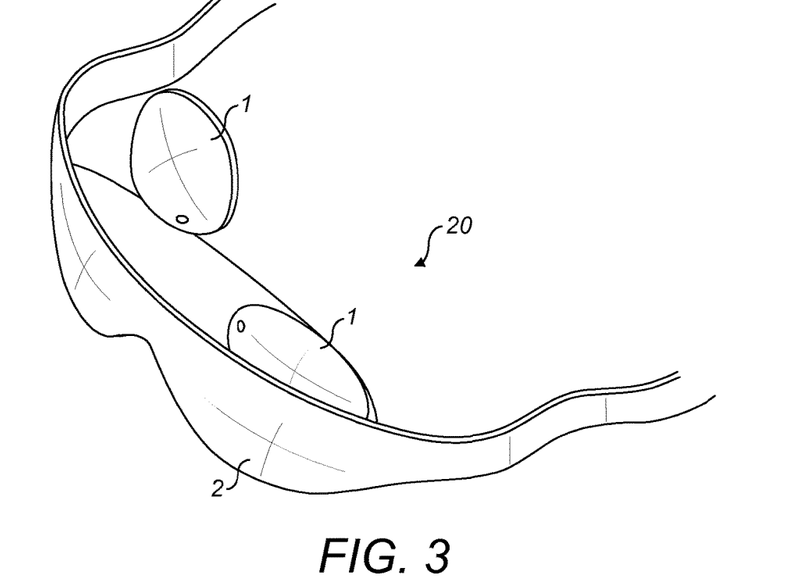
FIG. 3 illustrates a perspective view of an alternative holding element and cartridge.

An alternative embodiment of the present invention is shown in FIG. 3. The apparatus (20) bears many common features with the apparatus (10), which will not be further described. The difference of apparatus (20) is that the cartridge (1) is provided separately for each eye area. With this embodiment each cartridge (1) may be provided with independent features, such as a radiation source (e.g. OLED) and a power supply. This may be advantageous if only one eye requires treatment, or each eye requires different treatment regimes.

Figure 4:
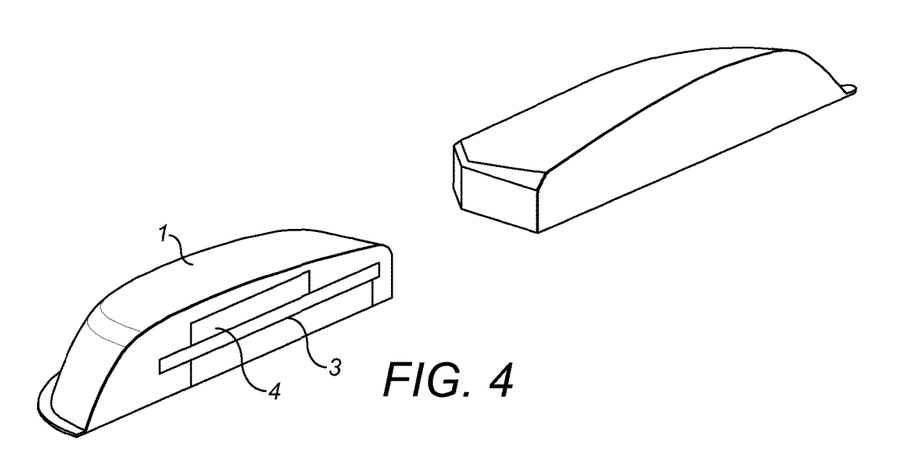
FIG. 4 illustrates a cross section through a cartridge.

FIG. 4 illustrates a cross-sectional cut away diagram of a cartridge (1) such as that shown in FIG. 3. The cartridge includes a radiation source, in this case an OLED (3) that is provided to one edge of the mount (6), and a power supply (4), in this case a battery.

Figure 5:
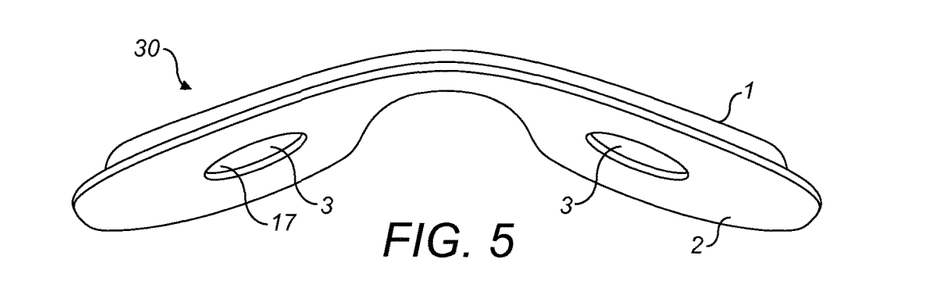
FIG. 5 illustrates another holding element and cartridge.

A yet further embodiment of the apparatus (30) of invention is shown in FIG. 5. In this embodiment the cartridge (1) is removably attached to a face of a holding element (2), rather than being inserted into a holding element. The holding element (2) has a pair of voids (17) corresponding to the eye areas of a user, such that radiation emitted by the radiation sources (3) on the cartridge may be directly received by the user. The apparatus (30) may have a securing element such as a strap (not shown) to fix the apparatus to a user's head. The cartridge (1) is adhered to the holding element (2) via adhesive tape, corresponding portions of hook and loop material, or the like.

Figure 6:
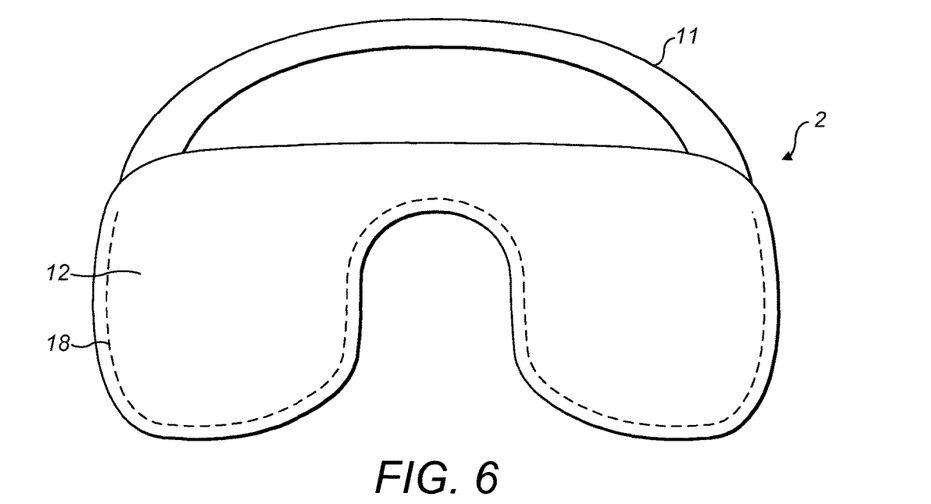
FIG. 6 illustrates another holding element.
Figure 7:
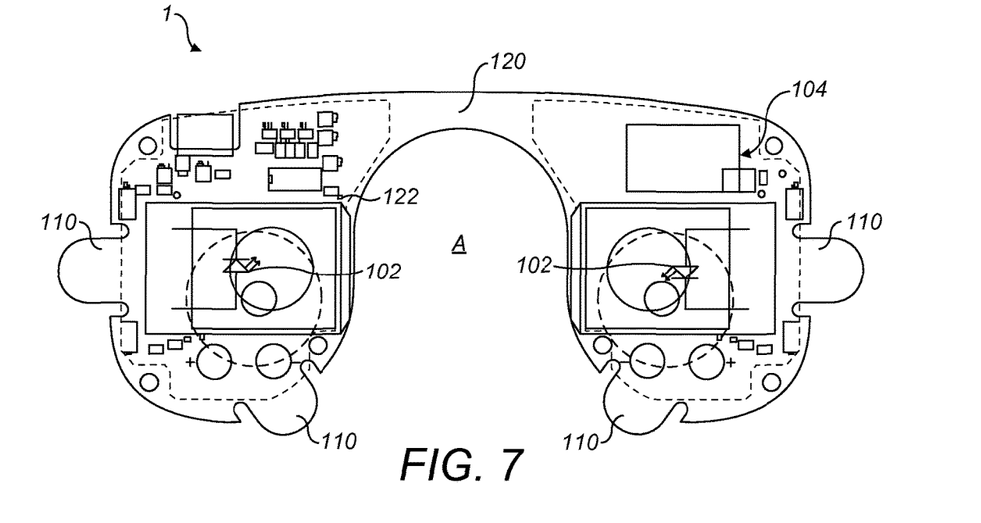
FIG. 7 illustrates a cartridge in the form of a PCB.
Figure 8:
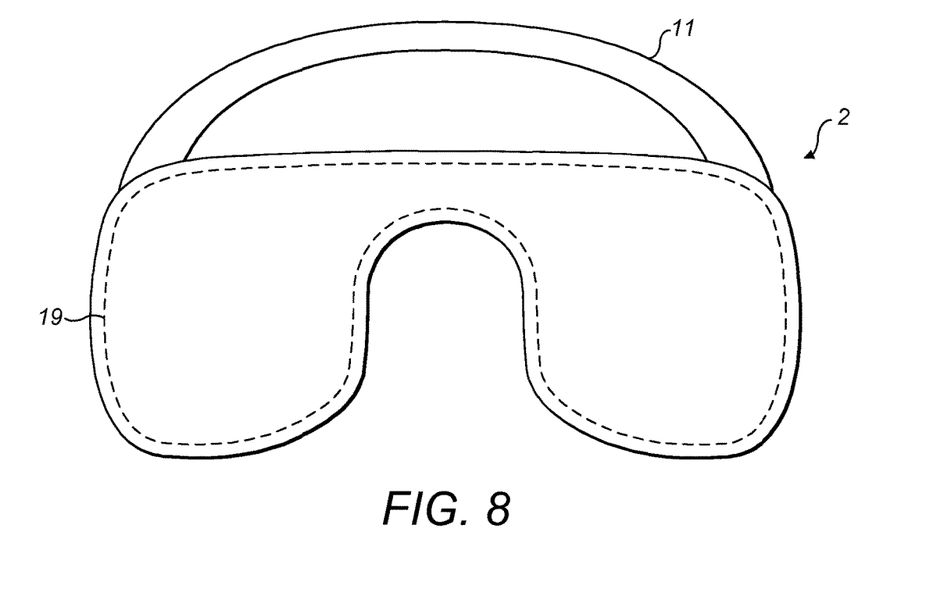
FIG. 8 illustrates the holding element of FIG. 6 with a cartridge in place.

FIGS. 6 to 8 illustrate a further example of the present invention. FIG. 6 illustrates a front view of a holding element (2). The holding element is generally the same as shown in FIGS. 2a and 2b. The dotted lines (18) illustrate stitching where a front body portion (12) and a rear body portion (13) are joined at side and lower areas to form a pouch therebetween (not shown). The pouch defined by the stitching (18) is shaped and sized to match the cartridge (1) shown in FIG. 7. Once inserted into the pouch, the cartridge (1) fits into the holding element (2) as depicted by the dotted lines (19) shown in FIG. 8.

FIG. 7 illustrates a printed circuit board (PCB) 120 supporting OLEDs 102 (for an apparatus having two OLEDs, one for each eye) and shaped to fit on or in an eye mask generally of the form illustrated in FIGS. 6 and 8 for example. The area A indicates generally where the user's nose may be when the mask is fitted to the user's face. FIG. 7 shows a processor 104 and four capacitive sensors 110, forming compliance sensors, spaced apart around the periphery of the PCB 120. The capacitive sensors extend from the PCB as flaps that may be folded against a user's face. There is also shown a power supply transistor chip 122 for controlling the supply of power to the OLEDs and the processor 104. The power supply may be a printed power source, which is a thin and flexible battery, such as those manufactured by Enfucell. In the embodiment shown in FIG. 7 there is a single processor 104, which additionally implements the functions of a clock, memory and output. It will be appreciated that the PCB shown in FIG. 7 may, as a whole, be considered as a mount for positioning the various elements with respect to the user. The PCB can be incorporated into the design of a mask, within the mask structure or adhered onto a mask structure. Forming the main electronic components onto a PCB structure may help enable a simpler, more cost effective manufacturing process. Of course it will be realised that the PCB or mount may be of any suitable shape to fit together with any suitable facial mask. The PCB or mount may have a different layout and design when used in another medical device such as a bandage or plaster, for example.

The cartridge, holding element and apparatus of the present invention locate in relation to the nose bridge of the user, are a self-contained, sealed device and is capable of illuminating for periods of more than 4 hours at a time. The cartridge is intended to be used during sleep to illuminate the user's retina and macular via a specifically configured window for optimum absorption. This device has many potential applications, specifically but not exclusively light therapy treatments for conditions such as diabetic retinopathy and macular degeneration.

The cartridge can be inserted into the mask-like attachment device (holding element) by the user on a regular basis, weekly or monthly for example. This means that in comparison with a device, rechargeable by the user, there is less likelihood of user errors in charging and insertion into the mask. It also means that the user, who is likely to be suffering from vision loss, does not need to worry whether they have inserted or charged the cartridge correctly.

The removable cartridge is also likely to ensure that the device is being used as prescribed, a user might forget to charge a rechargeable device or might forget to use it if it is not fully assembled by their bed while the batteries are being charged or are charging. The use of a rechargeable battery would most likely ensure the device was bigger and more costly and may mean that the cartridge device is less of a sealed unit.

A replaceable cartridge offers advantages because a new cartridge can be periodically inserted into the mask like attachment device, for example the cartridge may be replaced each week or each month ensuring that the treatment is consistent and the cartridge always operates effectively. This also enables the cartridge to be prescribed by a doctor or a vision specialist on an ongoing basis, a new cartridge being delivered to the user at regular intervals. A replaceable cartridge provides benefits to the user by ensuring the treatment device is always effective.

Locating the cartridge relative to the nose bridge enables the user to move during sleep while the illuminating feature remains positioned correctly and comfortably ensuring treatment is always being administered. It also means that the light treatment is correctly administered to the correct are i.e. the eyelid. It also means that the user can breath with ease due to the way in which the device is located not over the nose but to either side.

A particular version of the invention provides illumination by means of Organic Light Emitting Diodes (OLEDs). OLEDs are not only thinner and lighter they are also more flexible than LED's and LCD's. This means they can be attached easily to flexible substrates. OLEDs are brighter than LEDs. Because the organic layers of an OLED are much thinner than the corresponding inorganic crystal layers of an LED, the conductive and emissive layers of an OLED can be multi-layered. OLED's are less power hungry than LED's and have a much wider viewing range. OLEDs also produce less heat than a LED, and thereby less likely to harm or wake the user.

Various modifications to the detailed designs as described above are possible. For example, although the above embodiments have been described in relation to a facial mask type of apparatus, the apparatus could be configured to emit light radiation to another part of the body, such as in the form of a bandage or plaster. The cartridge and holding element can be shaped according to the body part to be treated.

Although the above-described cartridge has been described so as to be inserted into a holding element (FIGS. 2a, 2b, 3, 6) or onto the outer surface of a holding element (FIG. 5), a skilled person will realise that the cartridge could alternatively be attached to a holding element on the inner, skin-facing side of a holding element. For example, the cartridge could be releasable attached to an inner surface of a mask type holding element so as to position a radiation source directly adjacent the eyes of a user.

Although the above-described radiation source has been described as an OLED, other lighting devices may be used, for example an inorganic quantum dot based radiation source.

The invention further relates to the subject matter of the following paragraphs.

Paragraph 1. A replaceable cartridge providing one or more light source and an integral power supply located wholly within, or fixed to the cartridge such that when the cartridge is attached to the face by means of a separate releasable mask-like attachment device the light emitted by the cartridge is both directed towards one or more eye and the light source is positioned within the orbit of one or more eye and its position is controlled in relation to the nose bridge of the user.

Paragraph 2. A replaceable cartridge as described in paragraph 1 where the wavelength of the light emitted by the light source is between 480 and 550 nanometers.

Paragraph 3. A replaceable cartridge as described in paragraph 1 where the integral power supply is provided by one or more batteries.

Paragraph 4. A replaceable cartridge as described in paragraph 3 where the battery or batteries are rechargeable.

Paragraph 5. A replaceable cartridge as described in paragraph 4 where the power-source is provided by one or more printed batteries.

Paragraph 6. A replaceable cartridge as described in paragraph 1 where the cartridge includes means to position one or more light sources in relation to the nose bridge of the user.

Paragraph 7. A replaceable cartridge as described in paragraph 1 where the source of illumination is provided by one or more organic light emitting diodes.

Paragraph 8. A replaceable cartridge providing one or more light source capable of emitting light of a wavelength between 450 and 580 nanometers and an integral power supply located wholly within, or fixed to the cartridge such that when the cartridge is attached to the face by means of a separate releasable mask-like attachment device the light emitted by the cartridge is both directed towards one or more eye and the light source is positioned within the orbit of one or more eye and its position is controlled in relation to the nose bridge of the user.

Paragraph 9. A replaceable cartridge as described in paragraph 8 where the integral power supply is provided by one or more batteries.

Paragraph 10. A replaceable cartridge as described in paragraph 9 where the battery or batteries are rechargeable.

Paragraph 11. A replaceable cartridge as described in paragraph 10 where the power-source is provided by one or more printed batteries.

Paragraph 12. A replaceable cartridge as described in paragraph 8 where the cartridge includes means to position one or more light sources in relation to the nose bridge of the user.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A cartridge for operable connection with a holding device to form a phototherapy apparatus, the cartridge comprising:
   a radiation source for emitting radiation towards at least one eye of a user;
   a mount element for positioning the radiation source in a predetermined position relative to the at least one eye;
   wherein the cartridge is flexible to fit the face of the user;
   wherein the mount element comprises a locating portion configured for locating the cartridge at a predetermined position with respect to the face of the user, wherein the locating portion comprises a nose-bridge portion; and
   wherein the cartridge is configured to be insertable and held in the holding device;
   wherein the mount element mounts electronic components, and all of the electronic components that are mounted on the mount element are only located on opposite sides of the nose-bridge portion, without any electronic components being mounted on the nose-bridge portion.

2. A cartridge as claimed in claim 1, wherein the locating portion is configured to locate against a corresponding receiving portion of a holding device such that the cartridge can be located at the predetermined position with respect to the face of the user.

3. A cartridge as claimed in claim 1 wherein the locating portion is configured to locate the cartridge against a nose bridge of the user.

4. A cartridge as claimed in claim 1 wherein the radiation source is one or more OLEDs.

5. A cartridge as claimed in claim 1 wherein the radiation source is arranged to emit radiation having a wavelength in the range of 450 and 580 nanometers.

6. A cartridge as claimed in claim 1 further comprising a power source provided integrally with the cartridge.

7. A holding element for operable connection with a cartridge to form a phototherapy apparatus, the holding element comprising:
   a body portion arranged to hold a cartridge for emitting radiation towards at least one eye of a user;
   a securing element for securing the holding element against the user;
   a locating portion configured for locating the holding element at a predetermined position with respect to the face of the user, wherein the body portion in an assembled state comprises a front body portion and a rear body portion that are joined at side and lower areas to form a pouch therebetween having an opening for receiving the cartridge, wherein the cartridge is removably insertable into the pouch through the opening in the assembled state; and wherein the front and rear body portions are planar and flexible and arranged to hold the cartridge adjacent the front and rear body portions in a face to face configuration.

8. A holding element as claimed in claim 7 wherein the locating portion is configured to locate the holding element against a nose bridge of the user.

9. A holding element as claimed in claim 7 wherein the holding element is arranged in the form of a facial mask.

10. A holding element as claimed in claim 7 wherein the rear body portion comprises a void corresponding to the at least one eye such that radiation emitted by a cartridge operably connected with the holding element may be directly received by the user.

11. A holding element as claimed in claim 7 wherein the securing element is one or more straps.

12. An assembly comprising:
   a cartridge comprising a radiation source for emitting radiation towards at least one eye of a user, wherein the cartridge is flexible to fit the face of the user;
   a mount element for holding the radiation source;
   wherein the mount element comprises a locating portion configured for locating the cartridge at a predetermined position with respect to the face of the user; and
   a holding element for operable connection with the cartridge, comprising a body portion arranged to hold the cartridge in a predetermined position relative to the at least one eye, a securing element for securing the holding element against the user, and a locating portion configured for locating the holding element at a predetermined position with respect to the face of the user;
   wherein the body portion in an assembled state comprises a front body portion and a rear body portion that are joined at side and lower areas to form a pouch therebetween having an opening for receiving the cartridge, and wherein the cartridge is removably insertable into the pouch through the opening in the assembled state, and wherein the front and rear body portions are planar and flexible and arranged to hold the cartridge adjacent the body in a face to face configuration.

* * * * *